United States Patent [19]

Gignoux et al.

[11] Patent Number: 5,113,421
[45] Date of Patent: May 12, 1992

[54] METHOD AND APPARATUS FOR MEASURING THE THICKNESS OF A COATING ON A SUBSTRATE

[75] Inventors: Dominique Gignoux, Bethesda; Roland Gouel, Gaithersburg, both of Md.

[73] Assignee: Data Measurement Corporation, Gaithersburg, Md.

[21] Appl. No.: 602,272

[22] PCT Filed: May 12, 1989

[86] PCT No.: PCT/GB89/00518

§ 371 Date: Nov. 13, 1990

§ 102(e) Date: Nov. 13, 1990

[87] PCT Pub. No.: WO89/11095

PCT Pub. Date: Nov. 16, 1989

[30] Foreign Application Priority Data

May 13, 1988 [GB] United Kingdom ............... 8811459

[51] Int. Cl.$^5$ .................. G01B 15/02; G01N 23/223
[52] U.S. Cl. ............................ 378/50; 378/53; 378/54; 378/44; 378/45; 378/88; 378/89; 378/56; 250/382; 250/367
[58] Field of Search .................... 378/44, 45, 50, 89, 378/88, 90, 53, 56; 250/367, 382

[56] References Cited

U.S. PATENT DOCUMENTS

| 2,926,257 | 2/1960 | Friedman | 378/50 |
|---|---|---|---|
| 3,497,691 | 2/1970 | Chen | 378/50 |
| 3,562,525 | 2/1971 | Constantine | 378/50 |
| 3,952,197 | 4/1976 | Samson | 250/382 |
| 4,047,029 | 9/1977 | Allport | 378/90 |
| 4,350,889 | 9/1982 | Lisnyansky | 378/53 |
| 4,764,945 | 8/1988 | Tadahiro | 378/50 |
| 4,891,520 | 1/1990 | Ishibashi et al. | 250/367 |
| 5,029,337 | 7/1991 | MacKenzie et al. | 378/90 |

FOREIGN PATENT DOCUMENTS 0070974 2/1983 European Pat. Off. .
0197157 10/1986 European Pat. Off. .
0206735 12/1986 European Pat. Off. .
58-223047 12/1983 Japan .
59-195146 11/1984 Japan .
60-202339 10/1985 Japan .
62-3650 1/1987 Japan .

OTHER PUBLICATIONS

"The Application of Low Energy Gamma Sources to the Measurement of Strip and Coating Thickness in the Steel Industry", L. E. Taylor.

Primary Examiner—Janice A. Howell
Assistant Examiner—Kim-Kwok Chu
Attorney, Agent, or Firm—Evenson, Wands, Edwards, Lenahan & McKeown

[57] ABSTRACT

A method and apparatus for measuring simultaneously the thickness and the composition of a coating on a metal substrate. A first beam of radiation that produces a primary beam of photons is directed substantially perpendicularly to the surface of the coating. A first detector is positioned substantially perpendicularly to the surface of the coating to receive a first fluoresced beam. The photons having a first energy level representing a higher concentration element of the coating are selected. A first electrical signal is provided that is a function of the intensity of the photons having the first energy level. A second beam of radiation producing a second primary beam of photons is directed at an acute angle to the surface of the coating. A second detector is positioned substantially perpendicularly to the surface of the coating to receive a second fluoresced beam. The photons having a second energy level representing a lower concentration element of the coating are selected. A second electrical signal is provided that is a function of the intensity of the photons having the second energy level. From the first and second electrical signals, the relative composition of the elements of the coating and the thickness of the coating are simultaneously calculated.

16 Claims, 4 Drawing Sheets

METHOD AND APPARATUS FOR MEASURING THE THICKNESS OF A COATING ON A SUBSTRATE

FIELD OF THE INVENTION

This invention relates to the measurement of coating weight and relative concentration of a multi-element coating on a substrate, as well as to an apparatus for effecting such measurement. The method is also applicable when both the coating and the substrate contain the same element. Whether that element is an integral part of the coating chemistry of the element has migrated from the substrate to the coating through a process of diffusion; (for example, the migration of iron from a steel substrate into a zinc coating in galvannealed products).

BACKGROUND OF THE INVENTION

The problem of measurement of thin coatings of metals on metals has been resolved over several decades by using fluorescence. Specifically, such methods are used for the measurement of coatings of tin on steel (tinplate), or the coating of zinc on steel (galvanized steel). Other coatings may comprise metals such as nickel, chromium, aluminum, or brass, as well as many other metals. The substrate can be of steel, aluminum, brass or other metal. The range of coating density can vary considerably but are generally between a few grams per square meter up to several hundred grammes per square meter.

Known methods, such as disclosed in U.S. Pat. Nos. 2,711,480 and 2,926,257 to Friedman, and U.S. Pat. No. 2,925,497 to Bessen for example, are employed to measure the thickness of such a metal coating on another metal. The are generally based on either of the two following phenomena:

A. The fluorescence of the substrate material when illuminated by certain radiation. The thickness of the coating is then determined by its absorbing action on the fluorescence beam emitted by the substrate.

B. The fluorescence of the coating itself which is approximately proportional to the coating itself.

Sources of radiation used may be radioisotopes producing gamma rays of fixed energy or X-ray sources which produce a spectrum of radiation with the energy of each particle being at any level up to that represented in kiloelectron-volts by the kilovolt difference of potential across the X-ray tube.

In U.S. Pat. Nos. 2,711,480 and 2,926,257, Friedman describes fluorescence gauges to measure coatings on a substrate where he excludes the case of the coating and the substrate containing the same element.

In U.S. Pat. No. 2,711,480 Friedman describes the use of a monochromator (energy dispersive crystal), using the Bragg principle, between the fluorescence radiation and the detector, to discriminate between the fluorescence of the substrate and the coating. In U.S. Pat. No. 2,925,497, Beggen describes the use of a monochromator between the source of radiation and the coating to select preferentially the excitation energy from the radiation source. In both cases the use of a monochromator reduces significantly the radiation intensities involved in the measurement and accurate results can be obtained only if the measurements are made over several seconds which makes it difficult to use on a fast moving production line.

The problem is more difficult when the coating consists of two materials, and is even more difficult if the coating and the substrate contain the same element. In U.S. Pat. No. 4,764,945, Abe Tahidaro, (1988), addresses that difficult case by combining fluorescence measurements with Bragg diffraction measurements for a selected energy; (chrome Koc), performed at different angles, for the case of galvanneal products.

Again the main problem with this method is that the signals involved with the Bragg diffraction are extremely weak, and the time to make accurate measurements are very long especially for fast production lines. Also the apparatus is extremely complicated and mechanically slow requiring a detector rotating on an arm at accurate angles to measure the Bragg characteristic lines created by the crystalline structure of the material measured or the monochromator.

SUMMARY OF THE INVENTION

An object of the present invention is to provide a method to measure simultaneously the coating weight and relative concentration, especially when both the coating and the substrate contain the same element, with an efficient X-ray apparatus allowing the measurement on fast production lines.

It is an object of the invention to provide a measurement of the quantity of substrate that has migrated into the coating for the case of galvanneal products or similar products.

It is a further object of the invention to provide a measurement of coating thickness independent of the amount of substrate material that has migrated into the coating.

It is another object of the invention to provide a measurement that is fast enough to respond to product variations in a fast moving strip at a full production line speed.

According to the invention, there is provided a method of measuring the thickness and relative composition of a coating on a substrate comprising directing at least one incident beam of radiation at a predetermined acute angle of incidence towards the surface of a coating so that the major part of the beam of the incident photons or particles is stopped within the coating, causing fluorescence of the coating material, selecting the energy of the incident beam such that the major part of the flux of the incoming beam is stopped within the coating material and locating radiation detectors in such a position that only the emitted fluorescence beam or beams is or are accepted.

Thus the invention operates by the selection of a method which includes causing the fluorescence and observing said fluorescence in such a manner that only the coating will be affected and not the substrate. It is easier to provide for the primary beam to actually be stopped within the coating than to provide that the fluoresced beams emitted by the deeper layers of the coating material are mostly attenuated by the time that they reach the surface.

The invention also provides an apparatus for measuring the thickness of a coating material on a substrate, comprising a source of radiation adapted to produce at least one beam of radiation, means for directing the or each beam of radiation in a predetermined direction, towards a material to be irradiated, means for receiving the or each fluorescence beam of radiation emitted from said material and means for detecting and evaluating the received beam of radiation.

In one method of carrying out the invention, the source or radiation is directed so as to emit the or each beam of radiation at a predetermined angle to the surface of the coating.

In certain embodiments of the method of performing the invention, at least one of said beam or beams of radiation is directed at an angle of between 10° and 20° or 45° to the surface of the material.

In one embodiment of the invention, the source of radiation is an X-ray source, while in another embodiment of the invention, the source of radiation is a radio isotope.

According to a further embodiment of the invention, the detector comprises a proportional counter. In alternate embodiments of the invention, the detector comprises an ionization chamber, a scintillation counter or a solid state detector.

In a preferred embodiment of the invention, the detector comprises a combination of ion chambers provided with filters, one of which filters the fluoresced radiation above the fluoresced energy of the irradiated element and the other filtering the fluoresced radiation at an energy lower than that of the element. According to yet another advantageous embodiment of the invention, the detector comprises two ion chambers enclosed within a common housing with a common gas atmosphere and having different sets of electrodes.

Other objects, advantages and novel features of the present invention will become apparent from the following detailed description of the invention when considered in conjunction with the accompanying drawings.

DETAILED DESCRIPTION OF THE DRAWINGS

Figure 1:
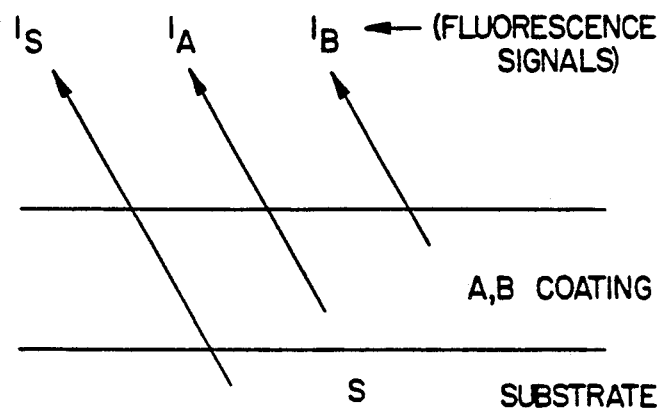
FIG. 1 shows schematically a substrate S on which is a coating material consisting of two elements, A and B.

As shown in FIG. 1 of the accompanying drawings, a substrate S is coated with a mixture of two elements, A and B. The problem then remains to find a way of calculating the total coating weight W and the proportion by mass (a) of the element A within the mixture of the elements A and B. The solution comprises measuring the radiation intensity emitted by the fluorescence of A, B and S, shown respectively as the quantities $I_A$, $I_B$ and $I_S$.

Figure 2:
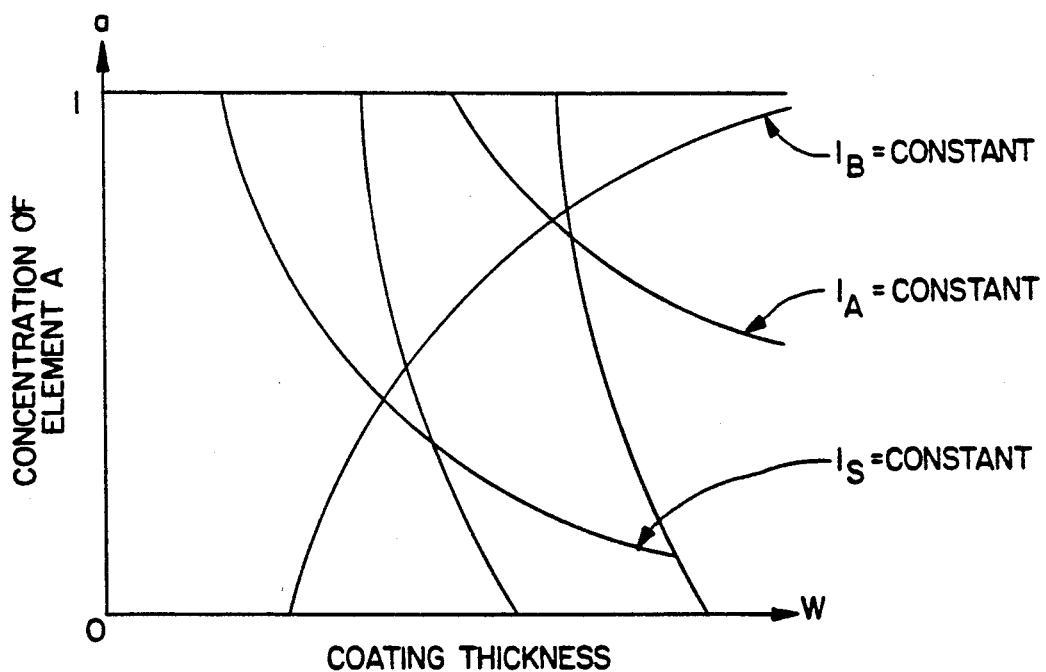
FIG. 2 is a graphical representation of the intensity levels I plotted against thickness W and concentration (a) of an element A in the coating.

In the example of FIG. 2, a certain value $I_A$ is obtained as well as a certain value of $I_B$. Two curves $I_A$ and $I_B$ corresponding to a constant value as a function of (a) and W are shown and intersect at such an angle that minor variations in the positions of the curves $I_A$ and $I_B$ due to errors in measurement do not result in a very large error in (a) and W.

Figure 3:
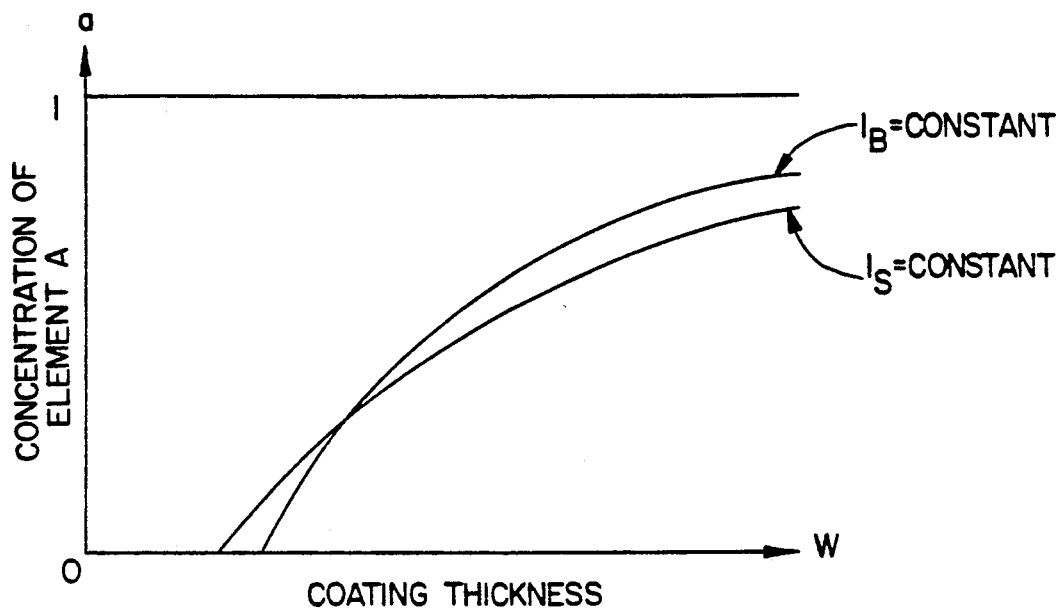
FIG. 3 is a graphical illustration of constant intensity levels plotted against coating thickness and concentration (a) of element A in the coating, where the coating contains the same element B as the substrate.

The particular case where one of the two elements in the coating is the same as that in the substrate, that is when B is the same element as S, presents some difficulty. In this case, as shown in FIG. 3, the diagram illustrates the intersection of the curves representing fixed values of $I_A$ and $I_S$.

It is immediately apparent that a slight error in measurement of $I_A$ or $I_S$ can result in very substantial errors in the value of (a) and W that are obtained by this method.

To understand the invention, it is desirable to recall the fundamental principle involved in the absorption of the radiation by matter. The intensity of radiation I, after passage of the radiation through a layer of thickness W in terms of mass per unit area, is given as a function $I_O$, the initial flux of radiation by:

$$I = I_O e^{-\mu W}$$

Figure 4:
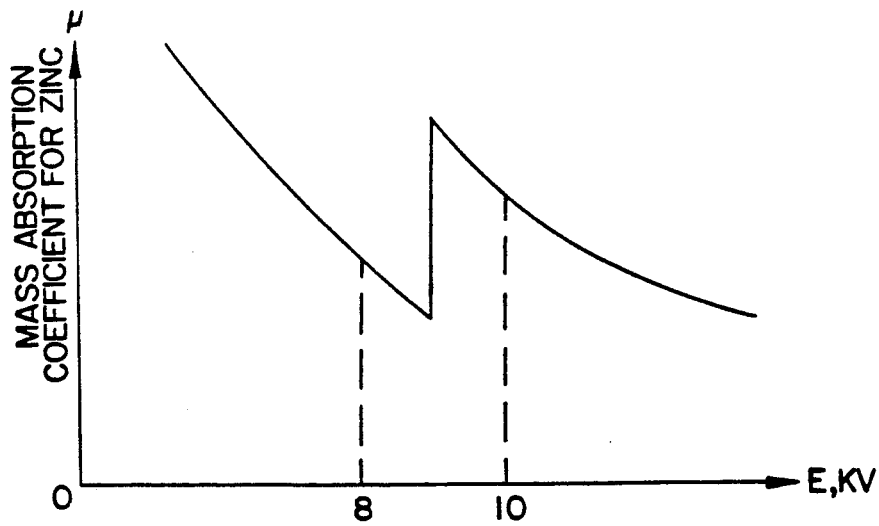
FIG. 4 is a graph in which mass absorption coefficient ($\mu$) is plotted against the energy level of the radiation.

The factor ($\mu$), mass absorption coefficient, varies with energy of the radiation. In the case of zinc, in the domain of energy of present interest, it varies according to that shown in FIG. 4. (Further explanation can be found for example, in Evans, Robley: The Atomic Nucleus, ISBN 0.89874.414.8 and Siegbahn: Alpha, Beta, Gamma Ray Spectroscopy, ISBN 0.7204.0083.X, and R. Tertian and F. Claise: Principles of Quantitative X-ray Fluorescence Analysis, ISBN 0.85501.709.0). This enables the calculation of the values of the thickness of material such that 1.8% or 13% of the radiation incident beam is not absorbed. For zinc it is as follows:

| Beam Energy, KV | Thickness in gm/m² for: | |
|---|---|---|
| | $1/I_O = 0.018$ | $1/I_O = 0.13$ |
| 7 | 464 | 232 |
| 9.658 | 1084 | 542 |
| 9.659 | 150 | 75 |
| 20 | 1055 | 528 |
| 35 | 5135 | 2568 |

It is, therefore, apparent that not only a certain energy of the incident radiation can be selected, but also an angle at which this beam is directed at the material so that a photon which would go through the entire material would actually have to go through a larger thickness due to the fact that the radiation beam is not perpendicular to the surface.

Figure 5:
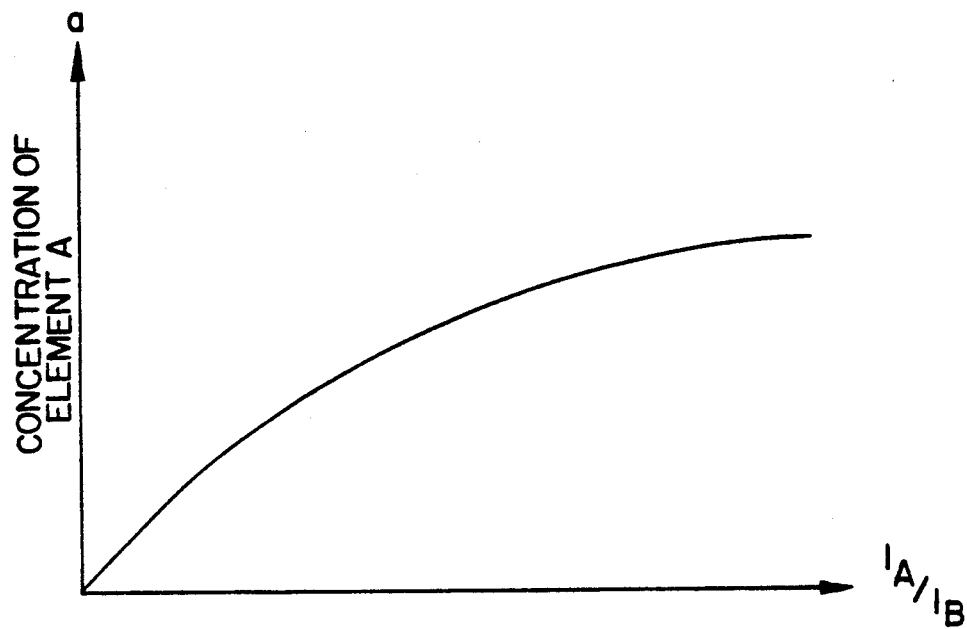
FIG. 5 is a graph of the value of the proportion by mass of one coating element plotted against the ratio of the fluorescence radiation levels of the elements of a coating.

If this is accomplished, then little of the fluorescence of the metal of the substrate is present in the output beam and the concentration (a) of A is related to the measurement of the quantity $I_A$ divided by $I_B$ as shown in FIG. 5. It is then possible to make a measurement of (a) easily. Measurement of the actual coating weight can be done using a second beam of radiation of different energy aimed at or perpendicular to the surface and collecting the values of $I_A$, $I_B$ and $I_S$ generated by that other beam. Only one of these values, in connection with the previously achieved evaluation of the quantity (a) is sufficient to provide the coating weight indication W.

Figure 6:
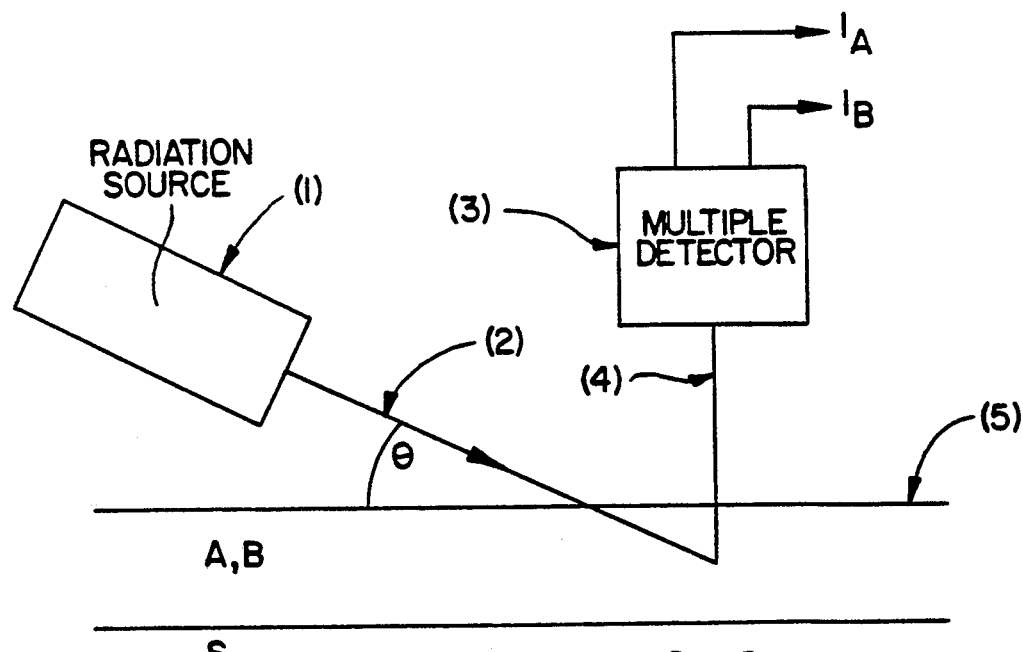
FIG. 6 is a simplified and schematic diagram of the apparatus for the performance of the method of the invention.

A particular embodiment of the invention is shown in FIG. 6, in which a source of X-ray radiation, 1, operating at two or more, predetermined, switchable energy levels (KV'S), is directed so as to emit a primary beam of radiation 2 at an angle $\theta$ which is preferably between 10° and 20° or 45° to the surface of the metal 5. One or more detectors 3, preferably perpendicular to the metal 5, receive the emitted fluoresced radiation 4. An alternative radiation source could be a radio isotope.

The detector may be a proportional counter, or an ionization chamber, for example, as described in Knoll, Glenn; Radiation Detection and Measurement, ISBN 0.471.49545.X or a combination of ion chambers provided with filters, one of which filters the fluoresced radiation above the fluoresced energy of the element under consideration and the other filtering the radiation at an energy lower than that of the element.

In this manner, by subtracting the output of one chamber from the output of the other, it is possible to obtain a measurement representing strictly the fluorescence of the element which is of interest.

An alternative method consists of combining two ion chambers or more, within one enclosure with a common gas, each with separate electrodes, each equipped with the proper radiation filter so as to isolate differentially the fluorescence energies $I_A$ and $I_B$ of the two elements A and B where $I_A$ is measured at a different energy level primary beam than $I_B$.

Figure 7:
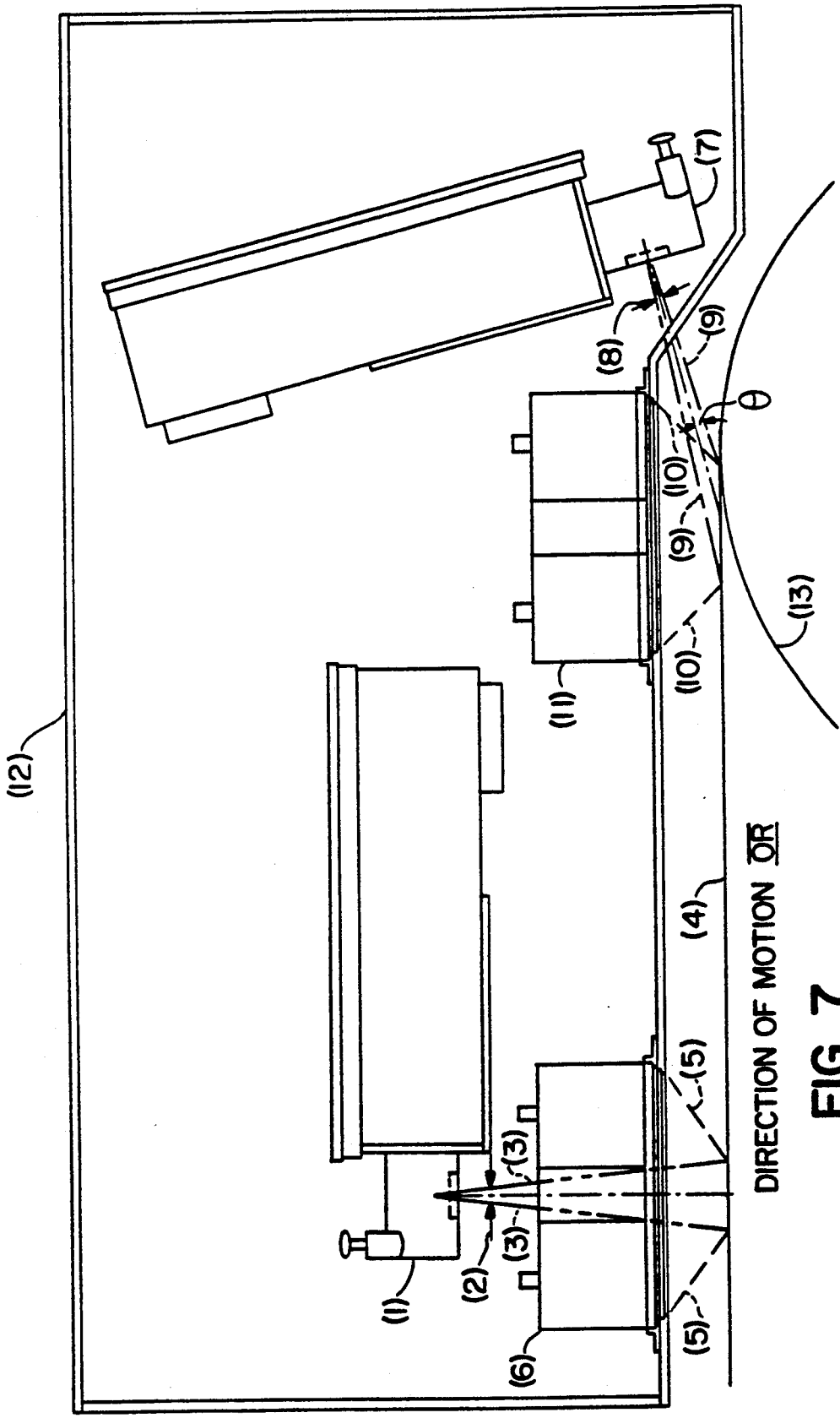
FIG. 7 is a schematic illustration of a preferred embodiment of an apparatus for carrying out the method of the invention.

An embodiment of the invention is shown in FIG. 7.

Refer also to FIG. 1 for the description of the material, where for this particular case element B in the coating is the same as the substrate.

An X-ray source (7) is directed to emit a beam of radiation (9) of selected energy level (KV) at angle ($\theta$) to the coating material strip (4), through a beam collimator (8).

A differential annular ion chamber detector (11), perpendicular to the coated material strip (4) intercepts the fluoresced and backscatters radiation (10) from the coated material strip (4) and discriminates the fluorescence of element B ($I_B$).

A second X-ray source (1) is directed to emit a beam of radiation (3) of selected energy level (KV), perpendicular to the coated material strip (4), through a beam collimator (2).

A differential annular ion chamber detector (6), perpendicular to the coated material strip (4), intercepts the fluoresced and backscattered radiation (5) from the coated material strip (4) and discriminates the fluorescence of element A. ($I_A$).

An enclosure (12) houses the X-ray sources (1), (7) and the detectors (6), (11).

The coated material strip (4) moves at high speed and is supported by roll (13).

A computer uses the measured signals $I_A$ and $I_B$ to simultaneously calculate the relative composition of the coating and the coating weight (or thickness).

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A method of measuring simultaneously the thickness and the composition of a coating on a metal substrate, comprising the steps:
   directing a first beam of radiation producing a first primary beam of photons substantially perpendicularly to the surface of the coating;
   positioning a first detector substantially perpendicularly to the surface of the coating to receive a first fluoresced beam and selecting from said first fluoresced beam the photons having a first energy level representing a higher concentration element of the coating, and providing a first electrical signal which is a function of the intensity of the photons having the first energy level;
   directing a second beam of radiation producing a second primary beam of photons at an acute angle to the surface of the coating;
   positioning a second detector substantially perpendicularly to the surface of the coating to receive a second fluoresced beam and selecting from said second fluoresced beam the photons having a second energy level representing a lower concentration element of the coating, and providing a second electrical signal which is a function of the intensity of the photons having the second energy level; and
   simultaneously calculating from the first and second electrical signals the relative composition of the elements of the coating and the thickness of the coating.

2. A method of measuring simultaneously the thickness and the composition of a coating on a metal substrate, comprising the steps:
   directing a first beam of radiation producing a first primary beam of photons substantially perpendicularly to the surface of the coating;
   positioning a first detector substantially perpendicularly to the surface of the coating to receive a first fluoresced beam and selecting from said first fluoresced beam the photons having a first energy level representing a higher concentration element of the coating, and providing a first electrical signal which is a function of the intensity of the photons having the first energy level;
   directing a second beam of radiation producing a second primary beam of photons at an acute angle to the surface of the coating;
   positioning a second detector substantially perpendicularly to the surface of the coating to receive a second fluoresced beam and selecting from said second fluoresced beam the photons having a second energy level representing a lower concentration element of the coating, and providing a second electrical signal which is a function of the intensity of the photons having the second energy level; and
   selecting the first and second energy levels and the acute angle so as to maximize an intersection angle between a first curve representing constant values of the first electrical signal and a second curve representing constant values of the second electrical signal, said first and second curves being plotted on a graph having one axis of coordinates representing thickness and another axis of coordinates representing relative composition of the elements of the coating; and
   simultaneously calculating from the first and second electrical signals the relative composition of the elements of the coating and the thickness of the coating.

3. An apparatus for measuring simultaneously the thickness and the composition of a coating on a metal substrate, comprising the steps:
- means for directing a first beam of radiation producing a first primary beam of photons substantially perpendicularly to the surface of the coating;
- a first detector positioned substantially perpendicularly to the surface of the coating to receive a first fluoresced beam, said first detector selecting from said first fluoresced beam the photons having a first energy level representing a higher concentration element of the coating, and providing a first electrical signal which is a function of the intensity of the photons having the first energy level;
- means for directing a second beam of radiation producing a second primary beam of photons at an acute angle to the surface of the coating;
- a second detector positioned substantially perpendicularly to the surface of the coating to receive a second fluoresced beam and selecting from said second fluoresced beam the photons having a second energy level representing a lower concentration element of the coating, and providing a second electrical signal which is a function of the intensity of the photons having the second energy level; and
- means for simultaneously calculating from the first and second electrical signals the relative composition of the elements of the coating and the thickness of the coating.

4. The method of claim 2, in which the source of radiation is directed so as to cause the coating to emit the emitted fluorescence at a predetermined angle to the surface of the coating.

5. The method of claim 4, in which at least one of said beams of radiation is directed at an angle of between 10° 45° to the surface of the material.

6. Apparatus of claim 3 wherein the source of radiation is an X-ray source.

7. Apparatus of claim 3, wherein the source of radiation is a radio isotope.

8. Apparatus of claim 3, wherein the detector comprises a proportional counter.

9. Apparatus of claim 3 wherein the detector comprises an ionization chamber.

10. Apparatus of claim 9, wherein the detector comprises a combination of ion chambers provided with filters, one of which filters the fluoresced radiations above the fluoresced energy of the irradiated element to be detected in the material, and the other filtering the fluoresced radiations at an energy lower than that of the fluoresced energy of the said element.

11. Apparatus of claim 10, wherein the detector comprises two ion chambers enclosed within a common housing, sharing a common gas, each equipped with a radiation filter, such that the difference between the outputs of the two ion chambers discriminates the fluorescence energy level of an irradiated element of the material.

12. Apparatus as claimed in claim 3, wherein the detector comprises scintillation counters.

13. Apparatus as claimed in claim 3, wherein the detector comprises solid state radiation detectors.

14. Apparatus as claimed in claim 3 wherein the detector comprises more than two ion chambers enclosed within a common housing, sharing a common gas, each equipped with a radiation filter, such that the difference between the outputs of any two ion chambers discriminates the fluorescence energy level of one of the irradiated elements of the material.

15. Apparatus as claimed in claim 10, wherein the detector comprises more than two ion chambers enclosed within a common housing, sharing a common gas, each equipped with a radiation filter, such that the difference between the outputs of any two ion chambers discriminates the fluorescence energy level of one of the irradiated elements of the material.

16. Apparatus as claimed in claim 11, wherein the detector comprises more than two ion chambers enclosed within a common housing, sharing a common gas, each equipped with a radiation filter, such that the difference between the outputs of any two ion chambers discriminates the fluorescence energy level of one of the irradiated elements of the material.

* * * * *